US010639082B2

(12) United States Patent
Lorio et al.

(10) Patent No.: US 10,639,082 B2
(45) Date of Patent: May 5, 2020

(54) METHODS AND APPARATUSES FOR DELIVERING A ROD TO A PLURALITY OF PEDICLE SCREWS

(71) Applicants: Morgan Packard Lorio, Bristol, TN (US); Mark A. Slaughter, Knoxville, TN (US)

(72) Inventors: Morgan Packard Lorio, Bristol, TN (US); Mark A. Slaughter, Knoxville, TN (US)

(*) Notice: Subject to any disclaimer, the term of this patent is extended or adjusted under 35 U.S.C. 154(b) by 0 days.

(21) Appl. No.: 15/391,799

(22) Filed: Dec. 27, 2016

(65) Prior Publication Data
US 2017/0105772 A1   Apr. 20, 2017

Related U.S. Application Data

(63) Continuation of application No. 14/356,478, filed as application No. PCT/US2012/063742 on Nov. 6, 2012, now Pat. No. 9,526,535.

(60) Provisional application No. 61/556,489, filed on Nov. 7, 2011, provisional application No. 61/639,832, filed on Apr. 27, 2012.

(51) Int. Cl.
A61B 17/70      (2006.01)
A61B 17/84      (2006.01)
A61B 34/00      (2016.01)
A61B 90/00      (2016.01)
A61B 17/00      (2006.01)

(52) U.S. Cl.
CPC ......... *A61B 17/7085* (2013.01); *A61B 17/70* (2013.01); *A61B 17/7002* (2013.01); *A61B 17/704* (2013.01); *A61B 17/7034* (2013.01); *A61B 17/7083* (2013.01); *A61B 17/848* (2013.01); *A61B 34/71* (2016.02); *A61B 2017/00867* (2013.01); *A61B 2090/3966* (2016.02)

(58) Field of Classification Search
CPC ................... A61B 17/7085; A61B 17/7034
See application file for complete search history.

(56) References Cited

U.S. PATENT DOCUMENTS

| 7,527,638 B2 * | 5/2009 | Anderson ........ A61B 17/00234 606/279 |
| 8,403,963 B2 * | 3/2013 | Garcia-Bengochea ...................... A61B 17/8897 606/246 |
| 2008/0015582 A1 * | 1/2008 | DiPoto ................... A61B 17/02 606/86 A |

(Continued)

*Primary Examiner* — Ellen C Hammond
(74) *Attorney, Agent, or Firm* — Michael R Shevlin

(57) ABSTRACT

Embodiments include a system that facilitates placement of a rod through receiving portions of screws placed along the spine. The system includes a rod and a cable detachably connectable to the rod to pull the rod through the receiving portions of the screws. Some embodiments include methods and devices for inserting a rod into a plurality of screws and for ex situ templating of a rod. These can include connecting a cable to a rod, inserting the cable through the plurality of screws, and using the cable to pull the rod into position. The methods of ex situ templating of the rod can include contacting a templating member to each of the screws so that a portion of the templating members replicate the relative positioning of the screws and shaping a rod to match the relative positioning of the portion of the templating members.

14 Claims, 9 Drawing Sheets

(56) References Cited

U.S. PATENT DOCUMENTS

2009/0171392 A1* 7/2009 Garcia-Bengochea ............... A61B 17/7002
  606/246
2010/0168803 A1* 7/2010 Hestad ................ A61B 17/708
  606/86 A

* cited by examiner

METHODS AND APPARATUSES FOR DELIVERING A ROD TO A PLURALITY OF PEDICLE SCREWS

CROSS-REFERENCE TO RELATED APPLICATIONS

This application is a divisional application of U.S. patent application Ser. No. 13/252,427, filed Oct. 4, 2011, which is a national stage application under 35 U.S.C. § 371 of PCT Application No. PCT/US2012/063742, filed Nov. 6, 2012, which claims the benefit of U.S. Provisional Patent Application No. 61/556,489, filed Nov. 7, 2011, and the benefit of U.S. Provisional Patent Application No. 61/639,832, filed Apr. 27, 2012, the entirety of both of which is incorporated by reference herein.

BACKGROUND OF THE INVENTION

Field of the Invention

This application relates to methods and devices for delivering a rod to a plurality of screws.

Description of the Related Art

The creation of a construct comprising a plurality of screws connected by a rod is used to treat a variety of ailments. In some cases, such a construct can be created in the spine, and can be used to fix the position of vertebrae relative to each other. The construct can be performed in a procedure in which a large incision exposes significant portions of the spine or other tissue into which the screws are positioned, or in a minimally invasive procedure through the use of smaller incisions to allow access to the targeted area.

While the use of the minimally invasive procedure causes less trauma to the patient, and thus is a less dangerous procedure with a quicker recovery time, the insertion of the rod through the screws is difficult, and frequently results in the need to revert to more invasive techniques during the operation. In light of these difficulties, new methods and devices are required to allow surgeons to more easily and effectively create such a construct with the minimally invasive procedure.

SUMMARY OF THE INVENTION

Certain embodiments of the present application relate to a method of delivering a rod to a plurality of screws, for example pedicle screws, and the instruments and implants associated therewith. The method can include, for example, advancing a cable through the heads of each of a plurality screws implanted into a plurality of adjacent vertebrae, and pulling the cable to advance a rod detachably connected to the cable through the heads of each of the screws. In some embodiments, a single portion of cable can be advanced into a patient through, along or at an angle to a first tower extending from a first screw, through the heads of each of the screws, and out of the patient through, along or at an angle to a second tower extending from a second screw. In some embodiments, the direction of the advance of the rod through the heads of the screws is the same as the direction of the advance of the cable through the heads of the screws.

Some embodiments relate to a method of passing a cable or flexible member through a plurality of adjacent screws. This can include using instruments to pass the cable from one screw to another and a cable that is connected to or includes a needle or other penetrating member to facilitate movement through tissue. In some embodiments, the cable can be detachably or non-detachably connected to the needle or penetrating member.

Some embodiments relate to a cable with features to facilitate placement of a rod through portions of adjacent screws placed along the spine. In some embodiments these features can include, for example, measurement markings. This marking can be visually detectable, or detectable through the use of other equipment, such as, for example, an x-ray machine. This marking can be used to determine the appropriate size and shape of a rod to be placed through the pedicle screws.

Some embodiments relate to a system or kit for advancing a rod through the heads of adjacent screws. The kit can include, for example, a penetrating member, a cable connectable to the penetrating member and to a rod, one or more pass devices configured to control the advance and direction of advance of the penetrating member, and a rod puller configured to engage and tension the cable to advance the rod through the heads of the screws.

One embodiment relates to a system to facilitate placement of a rod through receiving portions of screws placed along the spine. The system can include, for example, a rod, and a cable detachably connectable to the rod to pull the rod through the receiving portions of the screws.

In one embodiment, the cable has features to facilitate placement of the rod through the receiving portions of the screws. In one embodiment, the cable features include measurement markings.

In one embodiment, any of the above disclosed systems to facilitate placement of a rod through receiving portions of screws placed along the spine can further include a plurality of pedicle screws and extension sleeves extendable from each of the pedicle screws. In such an embodiment, the system can be configured to advance the cable through, along or at an angle to a first extension sleeve extending from a first pedicle screw, through the heads of each of the pedicle screws, and out of the patient through, along or at an angle to a second extension sleeve extending from a second pedicle screw. In one embodiment, any of the above disclosed systems to facilitate placement of a rod through receiving portions of screws placed along the spine can further include a penetrating member integral with or connectable with the cable to direct the cable through the receiving portions of the screws, and in one such embodiment, can further include one or more pass devices configured to control the advance and direction of advance of the penetrating member. In one embodiment, any of the above disclosed systems to facilitate placement of a rod through receiving portions of screws placed along the spine can further include a rod puller that can engage and tension the cable to advance the rod through the heads of the screws.

One embodiment relates to a system for making a spinal construct. The system for making spinal construct can include, for example, a plurality of spinal screws, each of which spinal screws can have a threaded shaft and a head having a receiving portion, a rod sized and shaped to be inserted into the receiving portions of the spinal screws, which rod can have a first end and a second end, a plurality of extension sleeves having an elongate member and defining a channel, each of which extension sleeves can extend out of a patient from a corresponding spinal screw when the spinal screws are placed within the patient, a cable detachably connectable to the rod, which cable can be directed along a path through the receiving portions of the spinal screws when the spinal screws are placed within the patient and can pull the rod into a desired location within the receiving portions, and a penetrating member that can direct the cable through the receiving portions of the screws.

In one embodiment of the system for creating the spinal construct, the rod can be connected to a first end of the cable, and the penetrating member is connected to a second end of the cable. In one embodiment of the system for creating the spinal construct, the penetrating member can be integral with a second end of the cable.

In one embodiment, the cable of any of the above disclosed systems for creating the spinal construct can further include a plurality of regularly spaced markers, and in one such embodiment, each of the markers is uniquely identified, and/or the markers are radiopaque.

In one embodiment, the cable of any of the above disclosed systems for creating the spinal construct can further include one pass device or a plurality of pass devices that can advance the penetrating member from a receiving portion of a first pedicle screw to a receiving portion of a second pedicle screw. In one such embodiment of the system for creating the spinal contrast, the one or more pass devices can include an operable control configured to allow a user to selectively engage the penetrating member and selectively advance the penetrating member.

In one embodiment, any of the above disclosed systems for creating the spinal construct can further include a penetrating member removal device. In one embodiment, any of the above disclosed systems for creating the spinal construct can further include a rod receiver that can receive the penetrating member and/or cable. In one embodiment, any of the above disclosed systems for creating the spinal construct can further include a rod puller configured to engage the cable and facilitate pulling of the rod into position within the receiving portions of the screws. In one embodiment, any of the above disclosed systems for creating the spinal construct can further include a cannula that can facilitate insertion of the rod through the receiving portions of the screws. In one embodiment, any of the above disclosed systems for creating the spinal construct can further include a delivery tube having a curved delivery portion that can direct delivery of the penetrating member into a receiving portion of a screw. In one embodiment, any of the above disclosed systems for creating the spinal construct can further include a hook or deflecting member that can be advanced into one or more of the extension sleeves to facilitate the advance of the penetrating member.

One embodiment relates to a method of delivering a rod to a plurality of spinal screws, comprising using any of the above disclosed systems.

One embodiment relates to a method of delivering a rod to a plurality of spinal screws. The method can include, advancing a cable through heads of each of a plurality spinal screws implanted into a plurality of adjacent vertebrae and pulling the cable to advance a rod detachably connected to the cable through the heads of each of the screws.

In one embodiment of the method of delivering a rod to a plurality of spinal screws, a single portion of the cable is advanced into a patient through, along or at an angle to a first tower extending from a first spinal screw, through the heads of each of the spinal screws, and out of the patient through, along or at an angle to a second tower extending from a second spinal screw.

In one embodiment of any of the above disclosed methods of delivering a rod to a plurality of spinal screws, the direction of the advance of the rod through the heads of the spinal screws is the same as the direction of the advance of the cable through the heads of the spinal screws. In one embodiment, any of the above disclosed methods of delivering a rod to a plurality of spinal screws can further include using a penetrating member to direct the cable through heads of each of the plurality of spinal screws, and can in one embodiment further include using one or more pass members to direct the penetrating member between adjacent spinal screws.

One embodiment relates to system for ex situ shaping of a rod for insertion into a construct having a plurality of pedicle screws. The system can include, for example, a first template member having a template rod receiving feature, which template member is sufficiently long that the template member can contact a pedicle screw located in a patient and the template rod receiving feature is located outside the patient, and a template rod, which template rod is sized to be received by the template rod receiving feature, and which template rod has dimensions and is made of materials to allow hand shaping of the template rod.

In one embodiment of the system for ex situ shaping of a rod for insertion into a construct having a plurality of pedicle screws, the template member can be sufficiently long such that the template member can contact a pedicle screw located in a patient and the template rod receiving feature is located outside the patient.

In one embodiment, any of the above disclosed systems for ex situ shaping of a rod for insertion into a construct having a plurality of pedicle screws can further include an insertion rod having a first end and a second end, which insertion rod is sized to be received by the template rod receiving features. In one embodiment, any of the above disclosed systems for ex situ shaping of a rod for insertion into a construct having a plurality of pedicle screws can further include a plurality of pedicle screws configured for insertion into a plurality of vertebrae. In one embodiment, any of the above disclosed systems for ex situ shaping of a rod for insertion into a construct having a plurality of pedicle screws can further include a first extension sleeve and a second extension sleeve, wherein each of the first and second extension sleeves has an elongate member having a channel. In one such embodiment, the channel of each of the first and second extension sleeves is sized and shaped to receive one or both of the first template member and the second template member.

In one embodiment, any of the above disclosed systems for ex situ shaping of a rod for insertion into a construct having a plurality of pedicle screws can further include a cable having a first end and a second end. In one such embodiment, the second end of the insertion rod can have a connection feature. in one such embodiment, the second end of the cable can connect with the connection feature of the insertion rod. In one embodiment, the second end of the cable is connectable to the insertion rod.

In one embodiment of the any above disclosed systems for ex situ shaping of a rod for insertion into a construct having a plurality of pedicle screws, the template rod receiving feature can include a circular cutout in the side of the first and/or second template members.

One embodiment relates to a method of ex situ shaping of a rod for insertion into a construct comprising a plurality of pedicle screws. The method can include, for example, contacting a first template member to a first pedicle screw inside a patient, wherein the first template member has a first template rod receiving feature, contacting a second template member to a second pedicle screw inside a patient, wherein the second template member has a second template rod receiving feature, using the first template rod receiving feature of the first template member and the second template rod receiving feature of the second template member to shape the insertion rod for insertion into the construct.

In one embodiment of the method of ex situ shaping of a rod for insertion into a construct comprising a plurality of pedicle screws, using the first template rod receiving feature of the first template member and the second template rod receiving feature of the second template member to shape the insertion rod for insertion into the construct includes using the first template rod receiving feature and the second template rod receiving feature to shape a template rod. In one embodiment, the method of ex situ shaping of a rod for insertion into a construct comprising a plurality of pedicle screws includes shaping the insertion rod to match the shape of the template rod.

In one embodiment of any above disclosed methods of ex situ shaping of a rod for insertion into a construct, the method includes validating the shape of the insertion rod by connecting the insertion rod to the first template rod receiving feature and to the second template rod receiving feature. In one embodiment of any above disclosed methods of ex situ shaping of a rod for insertion into a construct, the method includes connecting a template rod to the first template rod receiving feature. In one such embodiment, connecting the template rod to the first template rod receiving feature comprises longitudinally advancing the template rod into the first template rod receiving feature. In one embodiment connecting the template rod to the first template rod receiving feature includes laterally advancing the template rod into the first template rod receiving feature.

In one embodiment of any above disclosed methods of ex situ shaping of a rod for insertion into a construct, the method includes connecting the template rod to the second template rod receiving feature. In one such embodiment, connecting the template rod to the second template rod receiving feature includes longitudinally advancing the template rod into the second template rod receiving feature. In one embodiment, connecting the template rod to the second template rod receiving feature includes laterally advancing the template rod into the second template rod receiving feature.

DETAILED DESCRIPTION OF THE PREFERRED EMBODIMENTS

A rod can be delivered through a plurality of pedicle screws implanted in a plurality of adjacent vertebrae to rigidly or semi-rigidly connect two or more adjacent vertebrae. Although the screws described herein are referred to as pedicle screws, it will be appreciated that the screws may be placed in other spinal or non-spinal locations. The pedicle screws can each have a receiving portion configured for receiving the rod. The receiving portion can comprise, for example, a top, a bottom, opposed first and second sides, and opposed first and second openings. In some embodiments of a receiving portion, the top can comprise a piece such as an externally threaded set screw that is threadably engageable with internal threads on the first and second sides of the receiving portion. The top of the receiving portion can be additionally defined, for example, by the bottom of an extension tube. The receiving portion can be any of a variety of design, shape, or size, and can include, for example, a tulip head that pivots polyaxially relative to a threaded shaft such as illustrated in FIG. 1A.

Figure 1A:
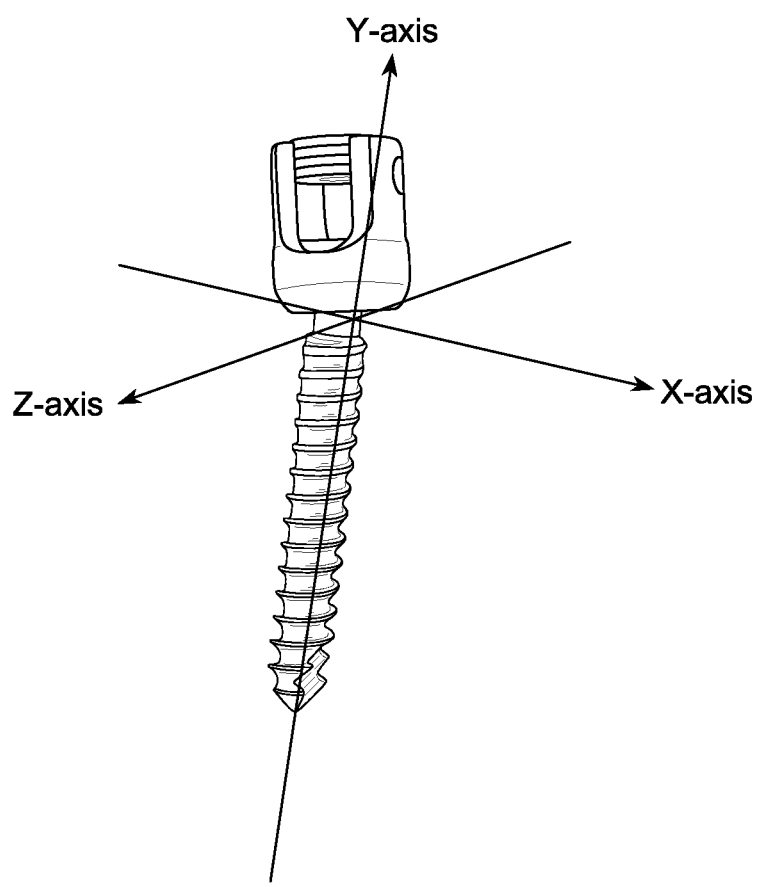
FIG. 1A depicts a perspective view of one embodiment of a pedicle screw.

FIG. 1A further depicts a coordinate system that can be used to describe the pedicle screw, and positions relative to the pedicle screw. The coordinate system includes, an X-axis, a Y-axis, and a Z-axis, each of which axes is normal to the other axes.

The pedicle screws can be located in various positions on several adjacent vertebrae. The screws can be, for example, linearly arranged along the axis of the spine and positioned in an inferior-to-superior orientation. The embodiments described below illustrate four adjacent pedicle screws, but it will be appreciated that fewer or more adjacent pedicle screws may be implanted.

A rod can be of any desired length, diameter, cross-sectional shape, or material. In some embodiments, for example, the material can comprise a biocompatible material, for example a metal such as titanium or stainless steel. The rod can be straight or curved. Additionally, the rigidity of the rod can vary based on the desired application. Thus, a rod can be sufficiently long to span one, two, three, four, five, six, seven, eight or any other desired number of vertebrae.

In some embodiments, a construct can be formed out of one or more pedicle screws and a rod. In some embodiments, a construct can be formed out of a plurality of pedicle screws and a rod connecting the plurality of pedicle screws.

Figure 1B:
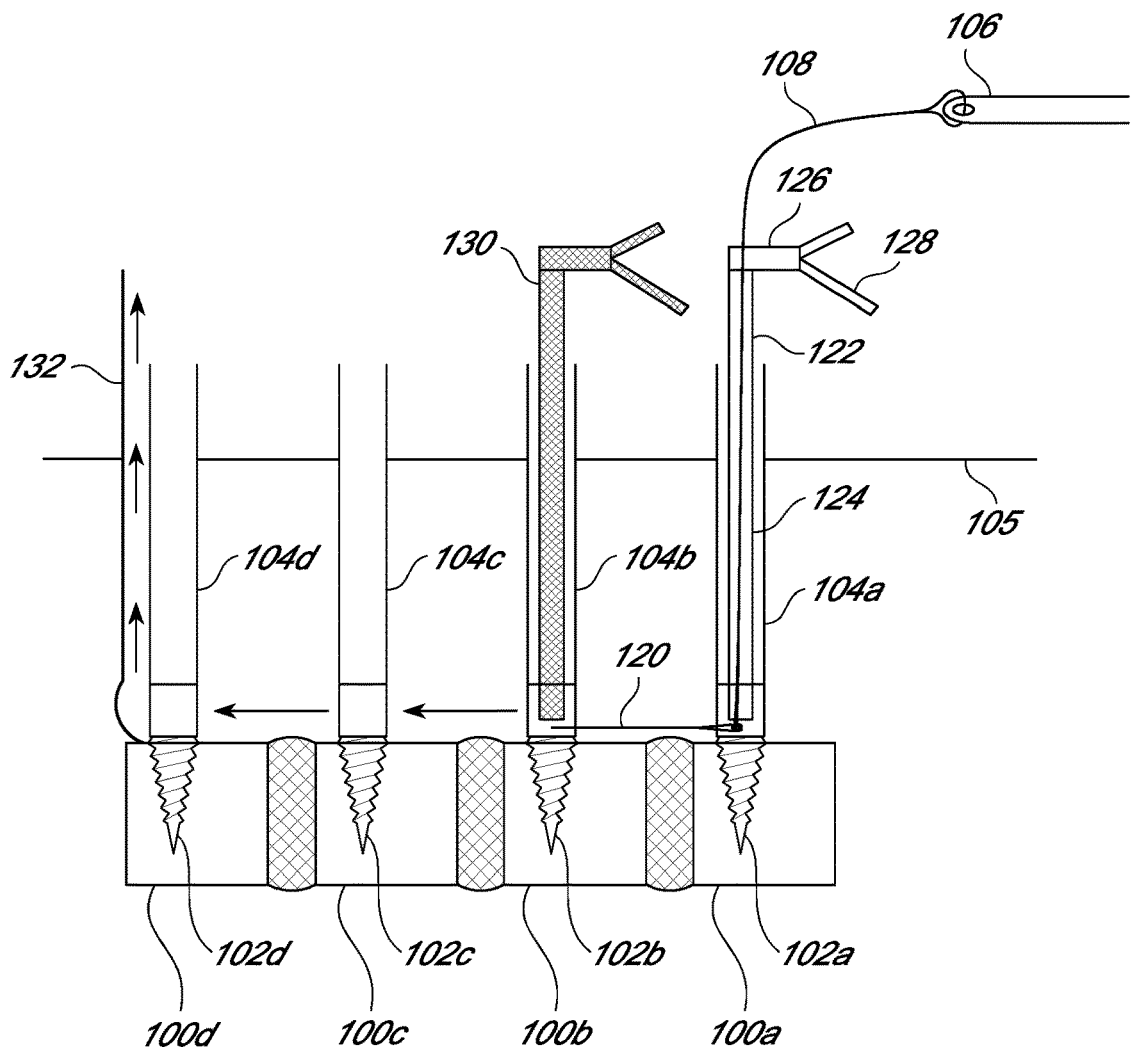
FIG. 1B depicts one embodiment of a method and devices for inserting a rod into a plurality of pedicle screws.

As shown in FIG. 1B, vertebrae 100*a-d* are accessed to allow placement of screws 102*a-d*, which can include pedicle screws, in the vertebrae 100*a-d*. Extension sleeves 104*a-d* are detachably coupled to the tulip heads of the screws 102*a-d*, and may be delivered with the screws 102*a-d* as the threaded shafts are screwed into the adjacent vertebrae 100*a-d*. The extension sleeves 104*a-d* extend posteriorly from the screws 102*a-d* through soft tissue and skin 105 to extend outside of the patient. The screws 102*a-d* and extension sleeves 104*a-d* can be any of the presently marketed screws and extension sleeves configured to connect one or several vertebrae.

As depicted in FIG. 1B, rod 106 is connected to cable 108. As described further below, the cable 108 is directed along a path passing through the receiving portions of the adjacent screws 102*a-d* and can be used to pull the rod 106 into the desired location within the receiving portions of the screws 102*a-d*. Cable 108 can be a flexible member capable of withstanding tensile forces associated with pulling a rod 106 through the receiving portions of screws 102*a-d*. Additionally, cable 108 can be configured to withstand bending and abrasion resulting from pulling rod 106 through the receiving portions of screws 102*a-d*. Cable 108 can include any material in any configuration, including any material and configuration that is capable of withstanding the forces and conditions associated with inserting rod 106, and can be for example, a natural material, a synthetic material, a metal, or any combination of these materials. In one embodiment, the cable 108 can comprise, for example, a fiber-tape type cable.

In some embodiments, cable 108 can additionally include a plurality of regularly spaced markers. The spacing of these markers can correspond to a standard unit of measure such as, for example, one-half centimeter, one centimeter, one-quarter inch, one-half inch, one inch, or any other desired spacing. The markers can be configured to be viewable after the cable is passed through the receiving portions of screws 102*a-d*. The markers may be viewable on exposed portions of the cable 108, or in some embodiments, markers may comprise a material that is viewable from within the patient's body, such as, for example, a radiopaque marker. In some embodiments, markers are identical. In some embodiments, each of the markers are unique so as to allow determination of the distance between screw 102*a* and screw 102*d* by reference to one or several of the unique markers on cable 108. Advantageously, addition of markers to the cable allows improved estimation of the length of the construct, which as depicted in FIG. 1B is the distance between screw 103*a* and screw 102*d*, and thereby better selection of the length of rod 106.

Figure 2:
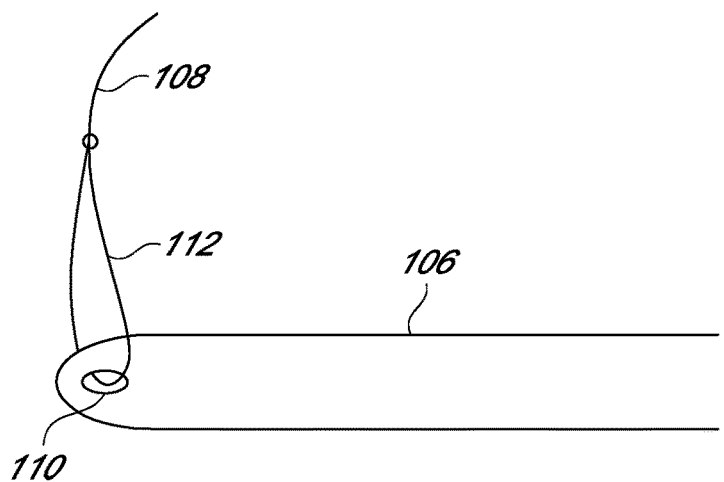
FIG. 2 depicts one embodiment of a method of connecting a cable to a rod.
Figure 3:
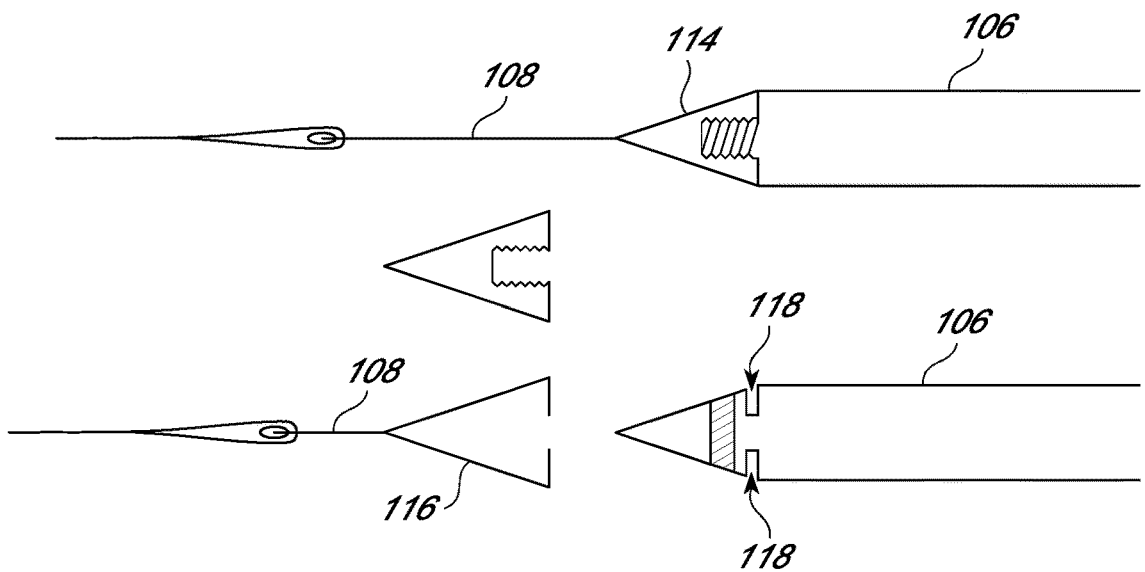
FIG. 3 depicts additional methods of connecting a cable to a rod.

The rod 106 can be connected to the cable 108 in any desired manner. FIGS. 2 and 3 depict several methods of connecting rod 106 to cable 108. As depicted in FIG. 2, cable 108 can be threaded through hole 110 in rod 106. Cable 106 can be secured by forming a loop 112 on cable 108 encircling a portion of hole 110 and rod 106. The loop 112 can be formed by securing the end of the cable to a midpoint of the cable, by, for example, tying a knot, adhesion, fusion or by a mechanical device, such as a clamp or a crimp-member. The loop 112 can be any desired length, including an eighteen inch loop, a twelve inch loop, a six inch loop, a three inch loop, a one inch loop, a loop fitted to the size of the rod, or any intermediate length. Advantageously, when a loop is sufficiently long so as to extend from the patient's body after insertion of rod 106, the cable 108 can easily be removed from the rod 106 by cutting loop 112.

As depicted in FIG. 3, cable 108 can be connected to rod 106 via a connector 114, 116. As also depicted in FIG. 3, the end of rod 106 configured to connect with cable 108 can likewise be configured to connect with connector 114. Thus, in embodiments in which connector 114 threads to rod 106, rod 106 can include a threaded portion configured to threadably engage with connector 114. Similarly, in embodiments in which connector 116 is configured for snapping or sliding engagement with rod 106, rod 106 can include slots 118 proximate to the end of rod 106 and configured for snapping or sliding engagement with connector 116.

Referring again to FIG. 1B, either before or after cable 108 is connected to rod 106, cable 108 may be connected to a penetrating member 120 in order to direct the cable 108 through the receiving portions of the screws 102*a-d*. Penetrating member 120 can be any object having sufficient strength and rigidity to penetrate tissue between pedicle screws 102*a-d* and to pull cable 108 between screws 102*a-d*, and having sufficient flexibility to navigate through or along the extension sleeves, tulip heads and other instruments described herein. A penetrating member 120 can be, for example, a needle, a rod, or any other member. A penetrating member 120 can comprise a variety of materials and designs, including, for example, a natural material, a synthetic material, a metal, or any other desired material. In one embodiment, a penetrating member 120 can be, for example, a flexible elongate needle made of a superelastic material such as nitinol. In one exemplifying embodiment, the penetrating member 120 can be a nitinol K-wire. Similar to above, cable 108 can be connected to penetrating member 120 using a variety of techniques. Thus, cable 108 can be connected to penetrating member 120 via a loop enclosing a hole or an eye on the penetrating member 120, can connect to the penetrating member 120 via a mechanical connector, can be fused to the penetrating member 120, can be part of the penetrating member 120, or can be connected to the penetrating member 120 in any other desired fashion.

As illustrated in FIG. 1B, the penetrating member 120 is passed through the receiving portion of screw 102*a*, through the receiving portion of screw 102*b*, through the receiving portion of screw 102*c*, and through the receiving portion of screw 102*d*. In one embodiment, the penetrating member is passed through the screws 102*a-d* in an inferior to superior direction. The penetrating member 120 may first be delivered into the proximity of the tulip head of screw 102*a* by passing penetrating member 120 through extension sleeve 104*a*, passing penetrating member 120 along the outside of extension sleeve 104*a*, passing penetrating member 120 through a separate cannula terminating proximate to the head of screw 102*a* (see FIG. 5 below), passing penetrating member 120 along the outside of a separate cannula terminating proximate to the head of screw 102*a*, passing penetrating member 120 through tissue with other suitable instruments, or any other desired method.

In one embodiment, the penetrating member 120 can be passed through the tulip head of screw 102*a*. A first pass device 122 may be utilized that comprises a first portion 124 configured for penetration into a patient's body and for selective engagement with the penetrating member 120, and a second portion 126 configured for user manipulation. A second portion 126 can comprise a handle with at least one operable control 128 that allows a user to selectively engage the penetrating member 120 and selectively advance the penetrating member 120 in a desired direction. A first pass device 122 can include features to allow advancement of the penetrating member 120 with a ratcheting mechanism.

A pass device can facilitate movement of a penetrating member 120 through the heads of screws 102*a-d*. A pass device can be brought into the proximity of one of the heads of screws 102*a-d* by inserting the pass device into and through an extension sleeve 104*a-d*, along an extension sleeve 104*a-d*, through or along a cannula, through a separate insertion point in patient's tissue, or in any other desired fashion.

The first pass device 122 illustrated in FIG. 1B can engage the penetrating member 120 and advance the penetrating member 120 through the tulip head of screw 102*a* and can further advance the penetrating member 120 towards the tulip head of screw 102*b*. As penetrating member 120 comes into the proximity of screw 102*b*, the penetrating member 120 can be manipulated so as to allow engagement of the penetrating member 120 by a second pass device 130 delivered through or along extension sleeve 104*b* and release of the penetrating member 120 by the first pass device 122.

Second pass device 130 can include the same features of first pass device 122 and can allow a user to pass the penetrating member 120 through the tulip head of screw 102b, and into the proximity of the head of screw 102c. As the penetrating member 120 comes into the proximity of screw 102c, the penetrating member 120 can be manipulated so as to allow engagement of the penetrating member 120 by a third pass device delivered through or along extension sleeve 104c and so as to allow release of the penetrating member 120 by the second pass device 130.

In some embodiments, the third pass device extending through or along extension sleeve 104c may be the first pass device after it has been removed from the first extension sleeve 104a. In this manner, two pass devices may alternatingly be used for additional vertebrae. When the penetrating member 120 reaches the last desired pedicle screw (as illustrated, screw 102d, though more or fewer than four screws and/or pedicle screws may be utilized), the penetrating member 120 can be removed from the patient. Removal of the penetrating member 120 can be facilitated by a penetrating member removal sleeve 132. A penetrating member removal sleeve 132 can be positioned superior to screw 102d and be configured to redirect a penetrating member 120 such that further advancement of the penetrating member 120 moves the penetrating member out of the patient's body. As illustrated in FIG. 1B, the removal sleeve may include a curved surface near its distal end to direct a tip of the penetrating member posteriorly. The surgeon may then grasp the penetrating member (either by hand or with an instrument) to pull the penetrating member out of the patient.

A penetrating member removal sleeve 132 can comprise a variety of shapes and materials. A penetrating member removal sleeve 132 can further be positioned proximate to the head of screw 102d by insertion of the penetrating member removal sleeve 132 through extension sleeve 104d, along the outside of extension sleeve 104d, through or along a cannula terminating proximate to the head of screw 104d, through a separate insertion point, or in any other desired manner.

Figure 4:
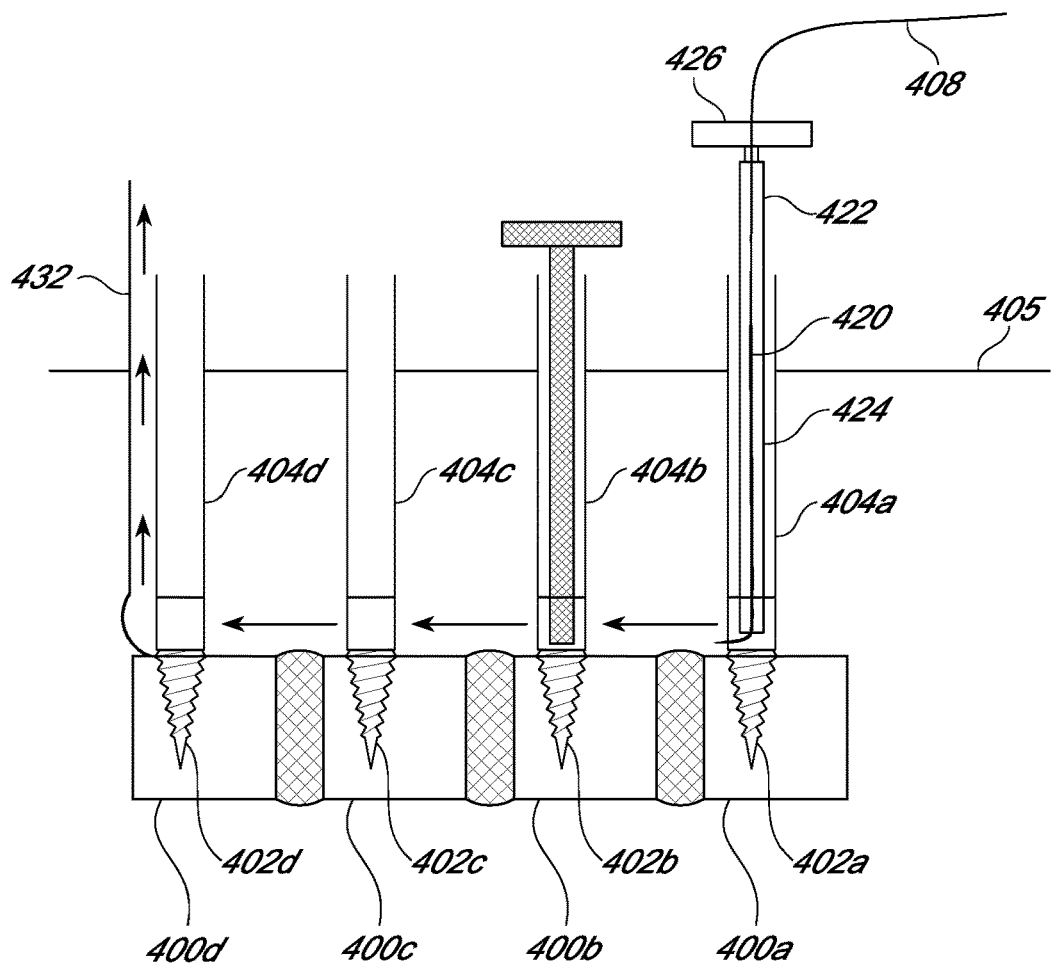
FIG. 4 depicts a second embodiment of a method and devices for inserting a rod into a plurality of screws.

FIG. 4 depicts another method of passing a penetrating member 420 connected to a cable 408 through the heads of screws 402a-d inserted into vertebrae 400a-d and accessible with extension sleeves 404a-d that pass through skin 405. As depicted in FIG. 4, a T-handle driver 422 selectively controls the advance and direction of advance of the penetrating member 420. The T-handle driver 422 can comprise a first portion 424 configured for penetration into a patient's body and for selective engagement with the penetrating member 420, and a second portion 426 configured for user manipulation. The second portion 426 can comprise a handle that allows a user to selectively engage the penetrating member 420 and selectively advance the penetrating member 420 in a desired direction.

Similar to the pass devices discussed above, the T-handle drive 422 can be positioned proximate to the head of screw 402a by insertion of the T-handle driver through or along extension sleeve 404a, through or along a cannula terminating proximate to the head of screw 402a, or through a separate insertion point.

After being positioned proximate to the head of screw 402a, the T-handle driver 422 can advance the penetrating member 420 through the tulip head of screw 402a, and towards the tulip head of screw 402b. A first guide device 430 can be positioned proximate to the tulip head of screw 402b, and can facilitate in the direction of penetrating member 420. A first guide device can be positioned proximate to the tulip head of screw 402b by insertion through or along extension sleeve 404b, through or along a cannula terminating proximate to the head of screw 402b, or through a separate insertion point.

As the penetrating member 420 nears the tulip head of needle 402b, the first guide device 430 can engage the penetrating member 420 to direct the advance of the penetrating member through the tulip head of screw 402b and towards the head of screw 402c.

As the penetrating member 420 nears the tulip head of needle 402c, a second guide device similar to the first guide device 430 and positioned in proximity to the tulip head of screw 402c can engage the penetrating member 420 to direct the advance of the penetrating member through the tulip head of screw 402c and towards the head of screw 402d.

As the penetrating member 420 nears the tulip head of needle 402d, a third guide device similar to the first guide device 430 and positioned in proximity to the tulip head of screw 402d can engage the penetrating member 420 to direct the advance of the penetrating member through the head of screw 402d. Although three guide devices are described herein, in some embodiments a single guide device may be used multiple times to direct the penetrating member through subsequent screws.

As cable 106 is connected to penetrating member 120, passage of penetrating member 120 through the heads of screws 102a-d pulls cable 106 through the heads of screws 102a-d. After passing of the penetrating member 420 through the head of screw 402d, the penetrating member 420 can be removed from the patient. Removal of the penetrating member 420 can be facilitated by a penetrating member removal sleeve 432 positioned superior to screw 402d and configured to redirect the penetrating member 420, as described above, such that further advancement of the penetrating member 420 moves the penetrating member out of the patient's body.

The advancing of the penetrating member 120, 420 through the heads of screws 102a-d, 402a-d and out of the patient's body advances the cable 108, 408 through the heads of screws 102a-d, 402a-d. After the cable is positioned, marks on cable 108, 408 can be used to measure the distance between screws 102a-d, 402a-d. This measurement can be used to select an appropriate rod length for use with screws 102a-d, 402a-d.

Figure 5:
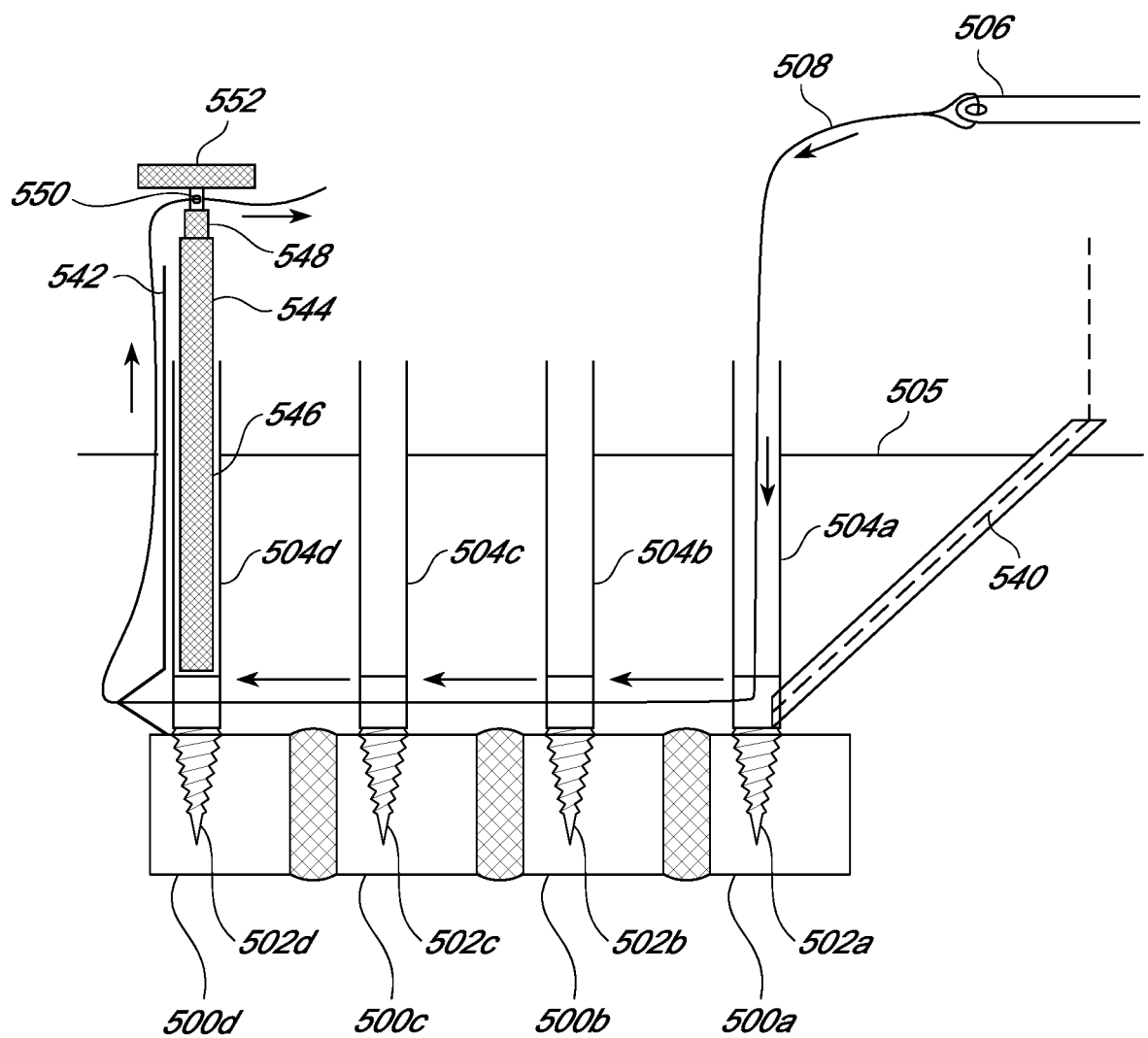
FIG. 5 depicts one embodiment of a method and devices for pulling a cable through a plurality of screws and for inserting a rod into a plurality of screws.

Rod 106 can then be attached to the cable (if not already attached) and be pulled through the tulip heads of screws 102a-d, 402a-d by advancing the cable 108, 408 through heads of screws 102a-d, 402a-d. The cable 108, 408 can be advanced through tulip heads of screws 102a-d, 402a-d using a variety of techniques and tools. One specific method of advancing the cable through tulip heads of screws is depicted in FIG. 5. FIG. 5 depicts screws 504a-d inserted into vertebrae 500a-d and accessible via extension sleeves 504a-d. A cable is passed through tulip heads of screws 504a-d. FIG. 5 depicts cable 508 passing through extension sleeve 504a, but as discussed above, cable 508 can pass through or along extension sleeve 504a, through or along cannula 540 terminating proximate to the head of screw 502a, or through a separate insertion point.

After passing through the heads of screws 502a-d, which can include, for example, pedicle screws, cable 508 further passes through rod receiver 542. The rod receiver 542 can include features configured to allow the penetrating member and/or the cable to pass through the rod receiver 542. In some embodiments, these features can be, for example, a hole or a slot. Rod receiver 542 is inserted proximate to the head of screw 502d. Similar to the penetrating member removal sleeve discussed above, the rod receiver 542 can be inserted proximate to the head of screw 502*d* through or along extension sleeve 504*d*, through or along a cannula, or through a separate insertion point. The rod receiver 542 can comprise features configured to abut with and stop of the advance of rod 506 after the rod has been advanced into position through the heads of screws 502*a-d*.

The cable 508 extends out of the patient's body, where the cable can be grasped to allow pulling of the rod 506 through the heads of screws 502*a-d*. As depicted in FIG. 5, cable 508 can be engaged by a rod puller 544. Rod puller 544 can engage the cable and facilitate pulling of the rod 506 into position. The rod puller 544 depicted in FIG. 5 comprises a first member 546 that inserts into proximity with the head of screw 502*d* and slidably engages with a second member 548 comprising a hole 550 and handle 552. The cable 508 can be inserted through hole 550 and affixed so that the elongation of rod puller 544 via sliding of the second member 548 away from vertebra 500*d* tensions cable 508 and advances rod 506 through the heads of screws 502*a-d*. In some embodiments, a single displacement of the second member may not be sufficient to completely advance the rod 506. In such an embodiment, after displacement of the second member 548, the second member may be moved towards vertebra 500*d*, and cable 508 can be readjusted relative to the first member 548 to allow additional advancement of the rod 506 by an additional, repeated displacement of the second member 548.

After the rod 506 is positioned, set screws or another securing mechanism may be delivered through the extension sleeves to secure the rod relative to the screws 502*a-d* and to lock the position of the tulip head relative to the threaded shaft. The cable 508 may be severed or detached from the rod, and the cable 508, extension sleeves 504*a-d*, rod receiver 542, and rod puller 544 are removed from the patient's body.

FIG. 5 additionally depicts the positioning of a cannula 540 for use in the insertion of a rod 506 through the heads of screws 502*a-d*. In some embodiments in which a long rod 506 is necessary, use of cannula 540 angularly positioned relative to the tulip head of screw 502*a* can facilitate the insertion of rod 506 through heads of screws 502*a-d*. In one embodiment, the cannula approaches the screw 502*a* at an angle from an inferior direction, and the penetrating member and cable are delivered through the cannula to the screw 502*a*. The pass or guide instruments as described above may then be used to advance the penetrating member and cable through subsequent pedicle screws in the same manner as previously described.

Figure 6:
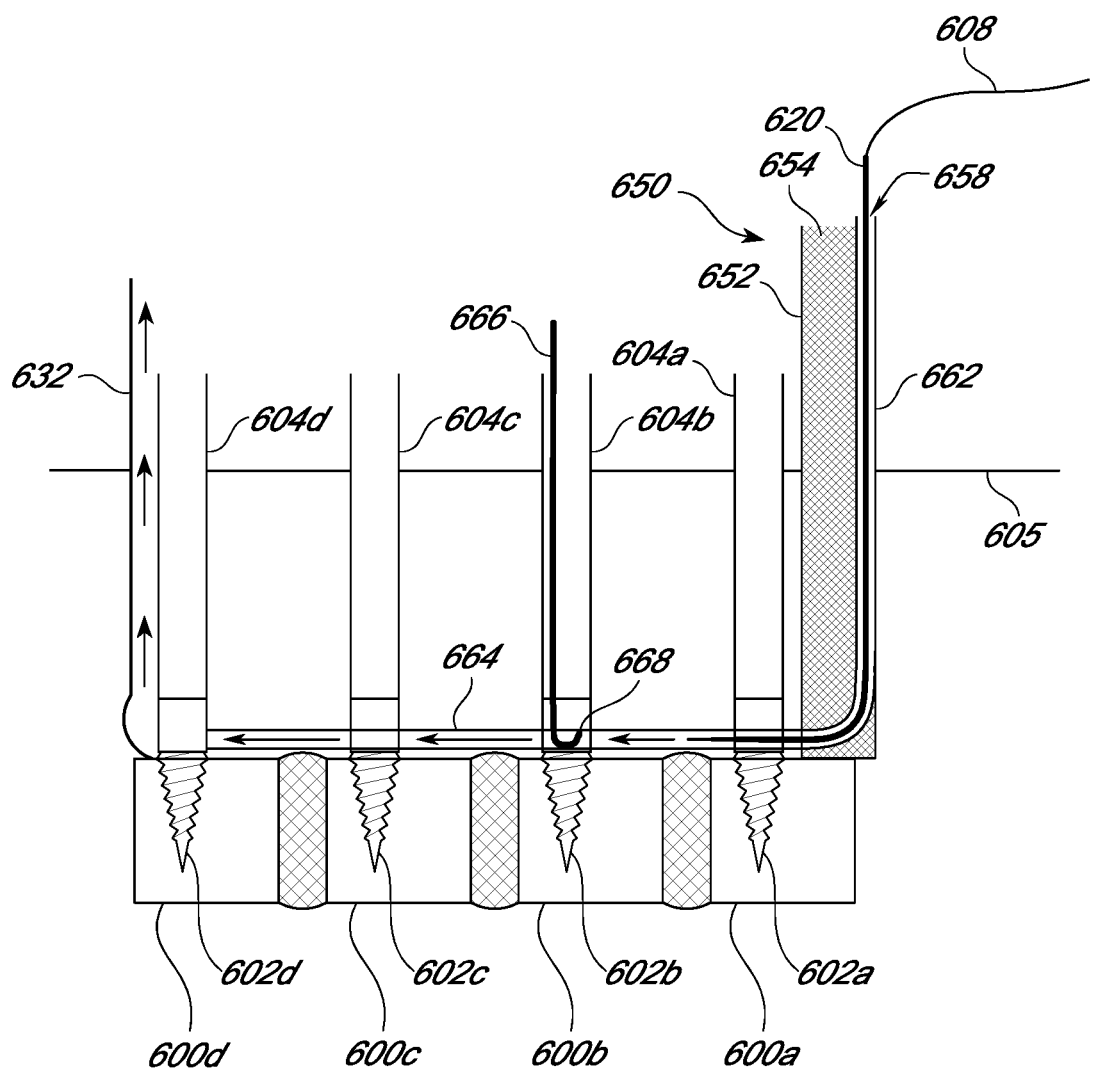
FIG. 6 depicts a third embodiment of a method and devices for inserting a rod into a plurality of screws.

FIG. 6, depicts an additional specific method of advancing the cable through tulip heads of screws, and features configured for advancing a cable through tulip heads of screws. FIG. 6 depicts screws 602*a-d*, which can include, for example, pedicle screws, inserted into vertebrae 600*a-d* and accessible via extension sleeves 604*a-d*, which extension sleeves 604*a-d* extend through skin 605. A delivery tube 650 is utilized to guide a penetrating member 620 such as a nitinol K-wire through tulip heads of screws 602*a-d*. A cable 608 attached to the K-wire may be guided through the tulip heads of screws 602*a-d* using the K-wire as discussed above.

As illustrated, the delivery tube 650 may be positioned inferior to the screw 602*a*. Delivery tube 650 can comprise a variety of shapes, sizes, and components. Delivery tube 650 shown in FIG. 6 includes an elongate body 652 having a first end 654 and a second end 656, and a delivery lumen 662 within the elongate body having a proximal receiving portion 658 and a curved delivery portion 660. In some embodiments, the second end 656 of the delivery tube 650 can be shaped to facilitate insertion into patent. Specifically, in some embodiments, the second end 656 can comprise a rounded or pointed portion to facilitate insertion of the delivery tube 650 into a patient.

In some embodiments, the body 652 of the delivery tube 650 can be configured for placement proximate to one of the extension tubes 604*a-d*.

The delivery tube 650 can be configured to receive penetrating member 620 and to direct the delivery of penetrating member 620 through the heads of screws 602*a-d*. The receiving portion 658 is configured to receive the penetrating member 620 and the curved delivery portion 660 is configured to direct the advance of the penetrating member 620 toward the tulip heads of the screws 602*a-d*.

In some embodiments, the delivery tube is also configured to receive a flexible tube 664 that may be advanced through delivery lumen 662 with the penetrating member 620. The flexible tube can be made of any desired material, and can be sized to allow the passage of the penetrating member 620, and/or of the cable 608 through an internal diameter of the flexible tube 664.

In one embodiment of a method of advancing the cable 608 through heads of screws 602*a-d*, the delivery tube 650 is inserted into a patient, and positioned so that the delivery portion 660 of the delivery tube 650 terminates proximate to the head of screw 602*a*. The flexible tube 664 is received by the receiving portion 658 of the delivery tube 650 and advanced through the lumen 662 and out the delivery portion 660 of the delivery tube 650. The flexible tube 650 can be used in different manners in different methods of advancing the cable through tulip heads of screws 602*a-d*. In one embodiment, the flexible tube 650 can be advanced ahead of the penetrating member 620, with the penetrating member 620, or behind the penetrating member. In some embodiments, advance of the flexible tube 650 ahead of the penetrating member can provide a per-established path to facilitate insertion of the penetration member 620. In some embodiments, advancing the flexible tube 650 behind the advance of the penetrating member 620 can provide additional directional control over the advance of the penetrating member 620.

The penetrating member 620 is received in the receiving portion 658 of the delivery tube 650 and advanced through the lumen 662 and out the delivery portion 660 of the delivery tube 650. The penetrating member 620 is advanced through the heads of screws 602*a-d*, and then contacts a penetrating member removal sleeve 632 positioned superior to screw 602*d* and configured to redirect the penetrating member 620, as described above, such that further advancement of the penetrating member 620 moves the penetrating member out of the patient's body. The flexible tube 664 can be removed to allow placement of the rod through the heads of screws 602*a-d*, or the flexible tube 664 can be left in place until after placement of the rod through the heads of screws 602*a-d*. The rod, which can be attached to the penetrating member 620 via the cable 608, is then positioned in the heads of screws 602*a-d* by advancing the cable 608 and the attached rod through the heads of the screws 602*a-d*.

In another embodiment, the direction of advance of the penetrating member can be controlled by movement of the delivery tube 650. In some embodiments, the advance of the penetrating member 620 through the heads of screws 602*a-d* can be facilitated by a hook 666 having an engaging end 668 advanced into one or more of the extension sleeves. In some embodiments, hook 666 can be configured for use in facilitating the advance of the penetrating member 620 by facilitating in the directional control of the advance of the penetrating member 620, for example, by lifting the penetrating member. Engaging end 668 can comprise a variety of shapes and sizes that allow for engagement with the penetrating member 620, cable 608, and/or rod. In some embodiments, for example, the engaging end 668 can have multiple hooks extending in different directions, multiple hooks longitudinally aligned along the hook, one or several notches, or any other desired shape.

Figure 7:
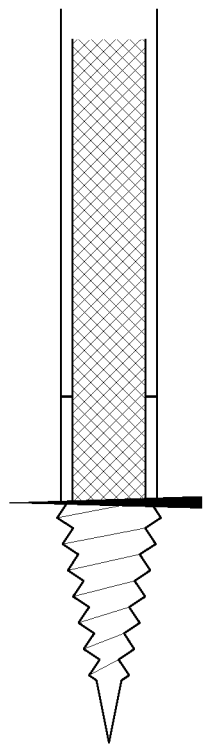
FIG. 7 depicts one embodiment of a tool configured to guide the advance of a penetrating member.

FIG. 7 illustrates another tool that may be used to deflect the penetrating member anteriorly. Such a tool may comprise an elongate body delivered through one of the extension sleeves used to push or otherwise deflect the penetrating member. Further tools (not shown) may be used to steer the penetrating member medially/laterally, such as by having tapered edges that when advanced through an extension sleeve, move the penetrating member to one side or another.

In some embodiments, the screws are linearly arranged, so that the receiving heads of the screws are aligned. In this embodiment, a straight rod 106 can be inserted through the receiving heads of the screws without bending the rod 106 or otherwise manipulating the rod 106 so that it is non-linear. In some embodiments, the receiving heads of the pedicle screws are not linearly aligned, which is referred to as non-linear alignment. In this embodiment, the rod 106 can be bent or otherwise manipulated so that the rod 106 is non-linearly shaped to correspond to the non-linear alignment of the screws and to fit through the receiving heads of the screws. This non-linear alignment of the pedicle screws can be caused, for example, by rotational displacements and/or linear displacements along one or more of the screw axes. These displacements can come from a variety of sources including, for example, inconsistencies in placement of the pedicle screws and/or variations in the geometry of the one or several vertebrae into which the pedicle screws are placed.

Figure 8:
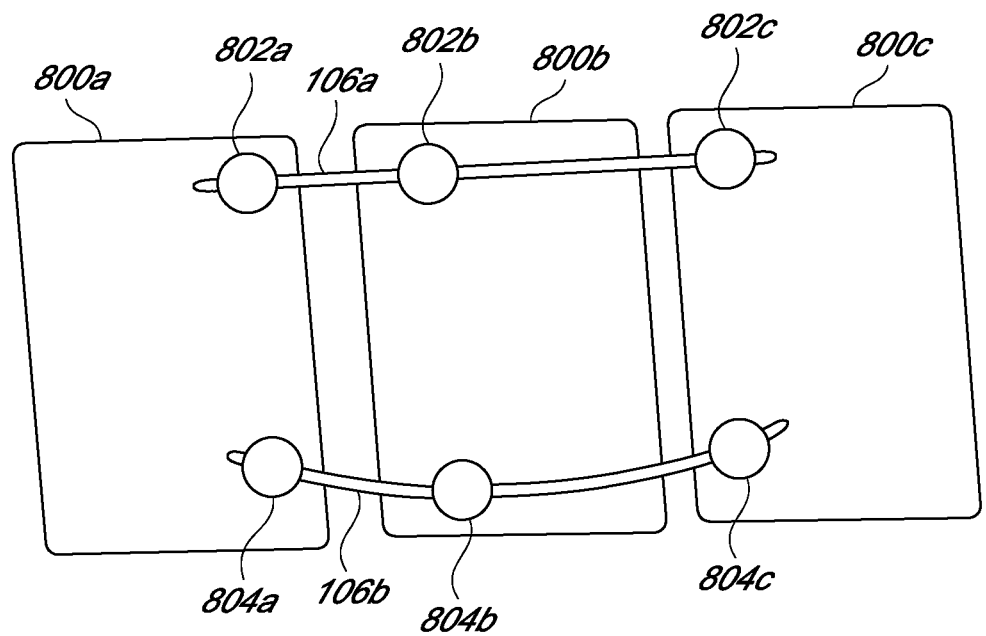
FIG. 8 depicts a first construct and a second construct, both having three screws connected by a rod.

FIG. 8 illustrates one embodiment of the non-linear alignment of a plurality of pedicle screws. As seen in FIG. 8 a plurality of screws 802*a-c* and 804*a-c*, which can be pedicle screws, are placed in vertebrae 800*a-c*. As FIG. 8 shows, screws 802*c* and 804*c* are not linearly aligned with screws 802*a-b* and 804*a-b*. Thus a rod 106*a*, 106*b* passing through the receiving heads of screws 802*a-c*, 804*a-c* will likewise be non-linear.

FIG. 8 additionally depicts a first single rod 106*a* and a second single rod 106*b* respectively connecting screws 802*a-c* and 804*a-c*. Due to the non-linear alignment of the screws 802*a-c* and 804*a-c*, the rods 106*a*, 106*b* connecting screws 802*a-c* and 804*a-c* are non-linear.

The rods 106*a*, 106*b* can be in situ shaped to match the non-linear alignment of the screws 802*a-c* and 804*a-c*, or the rods 106*a*, 106*b* can be ex situ shaped to match the non-linear alignment of the screws 803*a-c* and 804*a-c*. In some embodiments, the in situ shaping can be achieved with tools used in the creation of the construct, including, for example, the insertion tools, the extension sleeves, clamps, forceps, or any other desired tool. In some embodiments, the in situ shaping of the rod 106 can be achieved by the application of forces to the rod through soft tissue, such as, for example, the manipulation of the rod through the patient's skin.

In such shaping, the rod 106*a* is preferably accessed through existing incisions, such as, for example, the incisions for the extension sleeves. In some embodiments, the rod is accessed through the extension sleeves. However, in situ shaping of the rod 106 is difficult, and failure to properly shape the rod 106 can result in the ineffectiveness of the surgery and/or the construct, or can result in the creation of new incisions to allow access to the rod, which incisions can, for example, increase recovery time, or otherwise adversely affect a patient.

Figure 9:
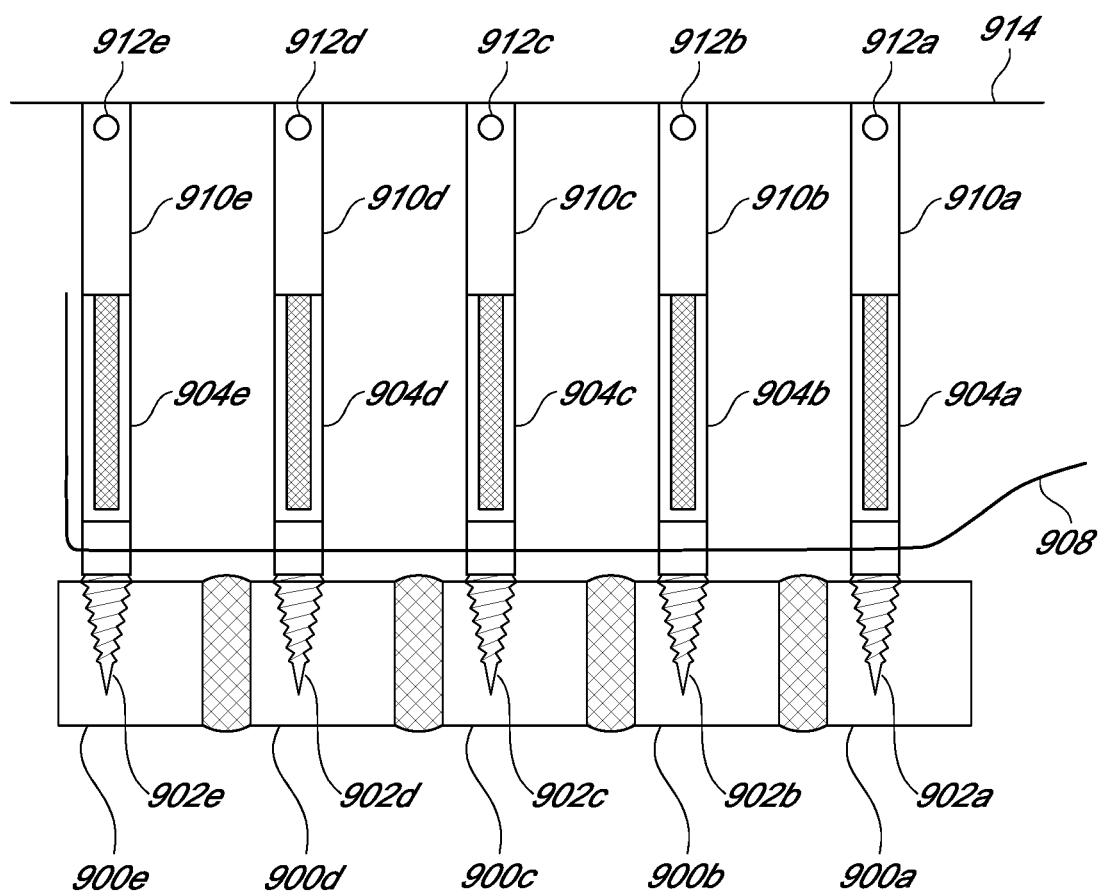
FIG. 9 depicts one embodiment of a method and devices for templating a rod.
Figure 10:
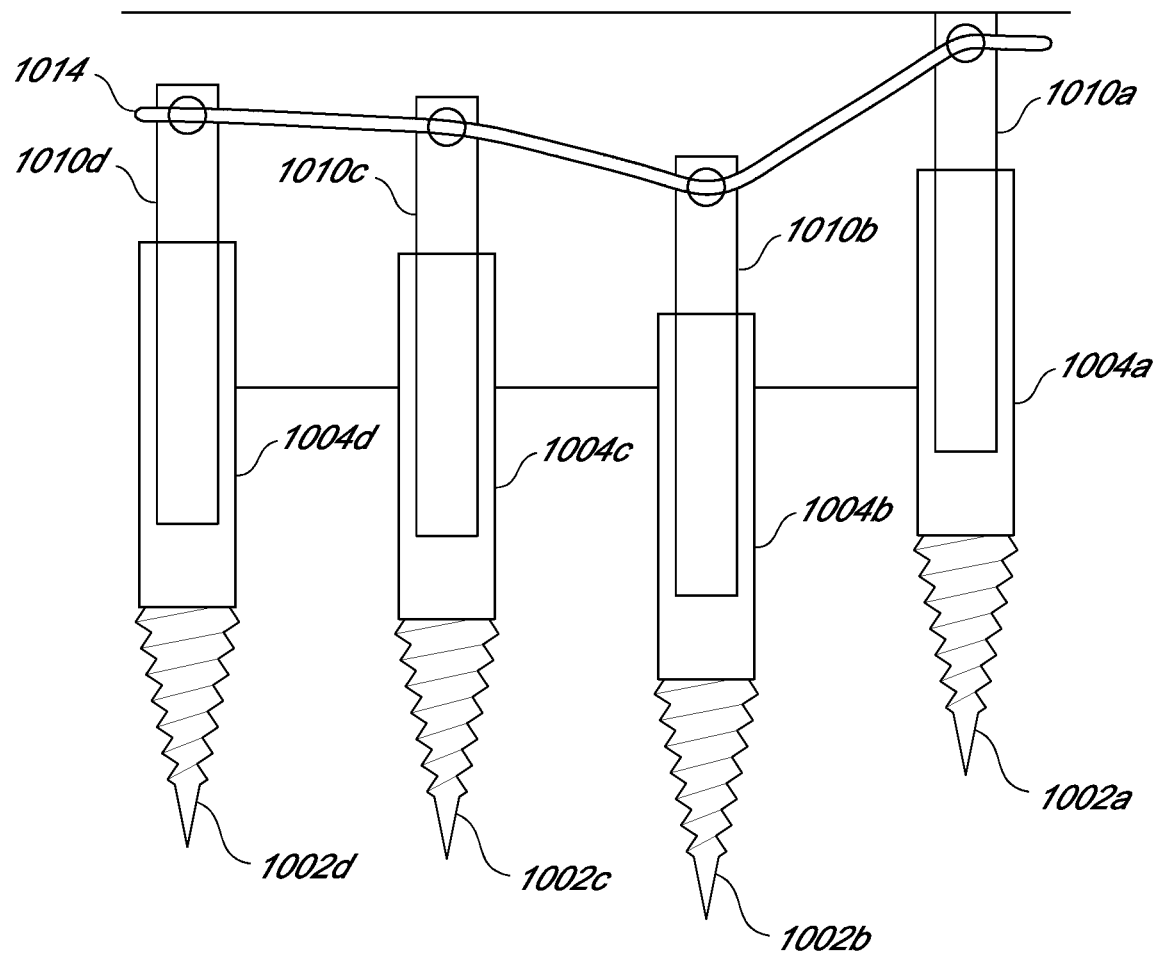
FIG. 10 depicts one embodiment of templated rod.
Figure 11:
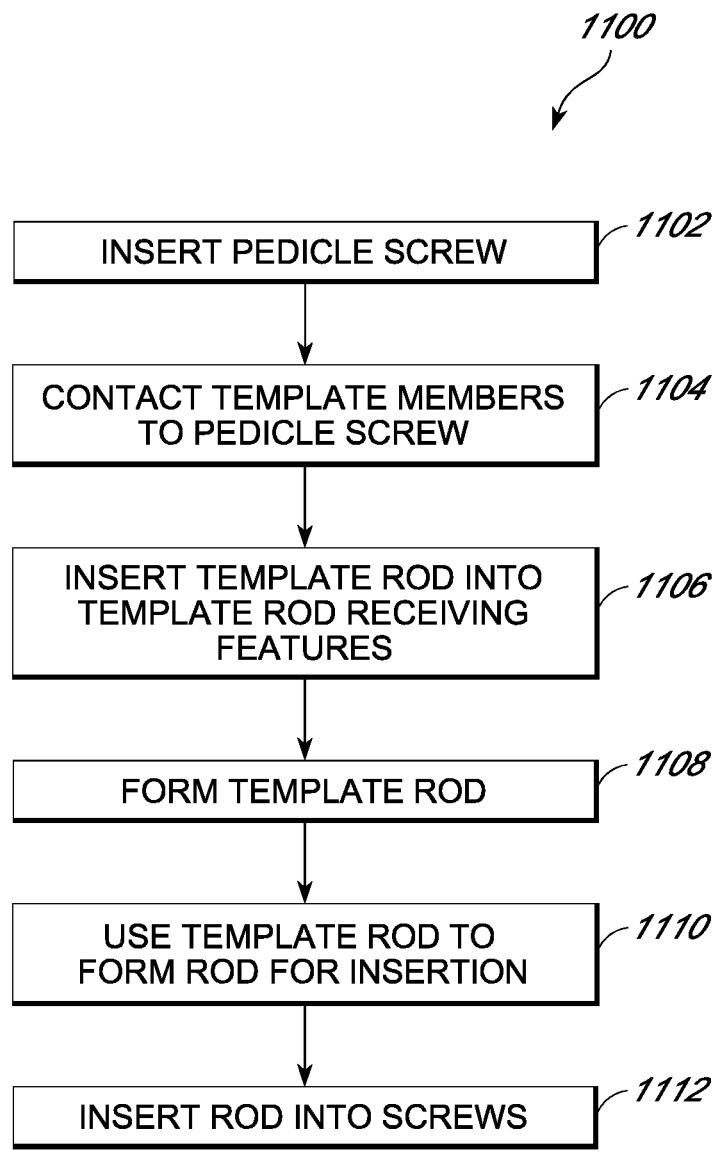
FIG. 11 is a flow-chart illustrating one embodiment of a process for templating a rod.

FIGS. 9, 10, and 11, shown below, depict systems and methods of ex situ shaping of the rod 106.

FIG. 9 depicts one embodiment of features and device for ex situ shaping the rod. After the rod has been shaped, the rod can then be advanced through one or several pedicle screws. FIG. 9 depicts screws 902*a-e* inserted into vertebrae 900*a-e* and accessible via extension sleeves 904*a-e*, which extension sleeves 904*a-e* extend through skin 905. FIG. 9 further depicts a cable 908 positioned through the head of each of the screws 902*a-e*.

FIG. 9 also depicts template members 910*a-e*. The template members 910*a-e* contact a portion of the screws 902*a-e*, such as, for example, the head of the screws 902*a-e*, and through the soft tissue of the patient, such as, for example, the skin. The template members 910*a-e* can be integral with the extension sleeves 904*a-e* or independent from and separately connected to the extension sleeves 904*a-e*. FIG. 9 depicts one embodiment in which the template members 910*a-e* are independent from the extension sleeves 904*a-e* and are positioned partially inside of the extension sleeves 904*a-e*.

The template members 910*a-e* can include template rod receiving features 912*a-e*. The template rod receiving features 912*a-e* can be configured to detachably connect a template rod 914 to the template members 910*a-e*. The template rod receiving features 912*a-e* can comprise, for example, a hole through the template members 910*a-e* that allows the template rod 914 to be longitudinally advanced through the template rod receiving features 912*a-e*, a cut-out that allows the template rod 914 to be laterally moved into the template rod receiving features 912*a-e*, or any feature capable of selectively securing the template rod 914 to the template member 910*a-e*. As depicted in FIG. 9, the template rod receiving features 912*a-e* comprise a circular cut-out in the side of the template members 910*a-e*.

The template rod 914 can comprise a variety of shapes and sizes. In some embodiments, the template rod 914 can comprise the rod 106 that is inserted into the screw, or a rod that is used to shape the rod 106 that is inserted into the screw. In some embodiments, the template rod 914 can have a size and shape approximating that of the rod 106 that is inserted into the screw. In some embodiments, the template rod 914 can comprise a variety of materials, including, for example, the same material as the rod 106. In some embodiments, the template rod 914 can comprise materials that facilitate templating, such as, for example, materials that have desired elastic properties, such as a low modulus of elasticity, materials that are easily deformed, such as materials with low yield strength, or any other desired materials. In some embodiments, the material selected for the template rod 914, combined with the design and dimensions of the template rod 914 can allow the template rod to be bent by hand, or by the application of 0.5 pounds of force, 1 pound of force, 2 pounds of force, 5 pounds of force, 10 pounds of force, 20 pounds of force, or any other desired or intermediate force level.

Returning again to the template members 910*a-e*, the template members 910*a-e* can be configured to contact the screws 902*a-e* so that the relative positioning of the template rod receiving features 912*a-e* corresponds to the relative positioning of the screws 902*a-e*. Such different relative positioning can be seen in FIG. 10 which is an illustration of how the different relative positioning of screws 1002*a-d* corresponds to the relative positioning of template members 1010*a-d* positioned in extension sleeves 1004*a-d*, and thereby to the shape of the template rod 1014.

Referring again to FIG. 9, in some embodiments, the template members 910*a-e* can be configured such that the both orientation and position of the template members 910*a-e* corresponds to the orientation and position of the screw 902*a-e* that the template member 910*a-e* contacts, and in some embodiments, the template members 910*a-e* can be configured such that the position of the template members 910*a-e* corresponds to the position of the screw 902*a-e* that the template member 910*a-e* contacts. In some embodiments, displacements and/or rotations of one screw relative to another screw along the X-, Y-, and/or Z-axis are reflected in the relative positioning of the template members contacting the screws. In some embodiments, template members 910*a-e* configured such that the position of the template member 910*a-e* corresponds only with the position (e.g. placement along one or more of the axes) of the screw 902*a-e* advantageously eliminates relative positioning distortions between the screws 902*a-e* and the template rod receiving features 912*a-e* arising from the rotational displacement of the screws 902*a-e* and the length of the template members 910*a-e*. In some embodiments, the length of the template members 910*a-e* is minimized, by for example, to the length necessary to pass through the patient's soft tissue, so as to minimize these relative positioning distortions.

In some embodiments, the template members 910*a-e* can be used to shape the template rod 914, and in some embodiments, the template members 910*a-e* can be used to determine the required length of the rod for insertion. Specifically, the length of the rod for insertion can be determined and/or estimated by determining the required length of the template rod 914 to connect the template members 910*a-e*. Advantageously, such a measurement can facilitate placement of a rod having the right length into the screws 902*a-e*.

A person of skill in the art will recognize that a variety of features and devices can be used in connection with the above described features to achieve ex situ shaping of rod for insertion into a plurality of screws, and that the present disclosure is not limited to the above enumerated features and devices.

A rod can be ex situ shaped using a variety of techniques. FIG. 11, depicts one embodiment of a process 1100 for ex situ shaping of a rod 106.

The process 1100 begins at block 1102 and the screws are inserted. In some embodiments, and as depicted in FIG. 11, the screws can comprise pedicle screws. The screws can be inserted into a variety of objects, including, for example, one or several vertebrae, one or several bones, or one or several bone pieces.

After the screws are inserted, the process 1100 moves to block 1104 and the template members are contacted to the screws. In some embodiments in which the template members are integral with the extension sleeves, the extension sleeves can be contacted with the screws as part of the screw insertion. In some embodiments in which the template members are independent from the extension sleeves, the template members can be placed inside the extension sleeves and can thereby contact the screws.

After the template members contact the screws, the process 1100 moves to block 1106 and the template rod may be connected with the template members via the template rod receiving features. In alternative embodiments, the template rod need not be connected with the template members in order to be shaped to match the template members. As discussed above, and as stated in FIG. 11, in some embodiments, the connection of the template members with the template rod can occur via the insertion of the template rod into template rod receiving features. This insertion can include longitudinal or lateral movement of the template rod into template rod receiving features. In some embodiments, this connection can further include the manipulation of template rod receiving features to securely connect the template rod to the template member.

In some embodiments, after the template rod is connected to the template member via the template rod receiving features, the process 1100 moves to block 1108 and the template rod is shaped. In some embodiments, the shaping of the template rod can comprise bending the template rod to match the relative positioning of the template rod receiving features. In some embodiments, this shaping can be performed before, during, or after the template rod is connected to the template member via the template rod receiving features. Specifically, in some embodiments, the template rod can be shaped and then connected to the template members via the template rod receiving features. In some embodiments, the template rod can be partially shaped before being connected to the template members via the template rod receiving features, and the shaping of the template rod can be finished after the template rod is connected to the template members via the template rod receiving features. In some embodiments, the shaping of the template rod and the connecting of the template rod to the template members can comprise iterative steps. Specifically, the template rod can be connected to a first template member via a first template rod receiving feature. The template rod can then be shaped to allow the template rod to be additionally connected to a second template member via a second template rod receiving feature, and the template rod can be attached to the second template via the second template rod receiving feature. The process can then be repeated until the template rod is connected to all of the template members. In some embodiments, this shaping can be performed concurrently with the contacting of the template members to the screws.

After the template rod has been shaped to match the relative positioning of the template rod receiving features, the process 1100 moves to block 1110 and the template rod is used to shape the rod for insertion into the screws. The shaping of the rod for insertion into the screws can be performed in a variety of ways, including, for example, using the shaped template rod as a pattern to shape the rod for insertion. As discussed above, in some embodiments, the template rod can be the rod that is inserted into the screws. In such an embodiment, the process 1100 may not include a step in which the template rod is used to shape the rod that is inserted into the screws.

In some embodiments, the shaping of the template rod can additionally include the creation of a template rod having the required length to connect all of the screws forming the construct. In some embodiments in which a cable comprising markers is inserted through the screws, the markers can be used to measure the length of the construct, which measurement can be used to shape the template rod to the desired length. In some embodiments, the template members can be used to measure the length of the construct, which measurement can be used to shape the template rod to the desired length.

After the rod for insertion into the screws has been shaped, the process 1100 moves to block 1112 and the rod is inserted into the screws. The insertion of the rod can be performed using any desired technique, and in some embodiments, the insertion of the rod can be performed using some or all of the above discussed methods of inserting a rod.

A person of skill in the art will recognize that the above recited process 1100 can include more or fewer steps than those listed above. A person of skill in the art will further recognize that the order of the above listed steps can be changed, and that the present disclosure is not limited to the above listed steps or order of steps.

Although the methods and devices are described above with respect to a use with the spine, the device can be used with other portions of the body and in other procedures, including, for example, any time in which portions of a bone are connected. Further, although the methods described above relate to connecting four vertebrae, different embodiments of the methods can be used to connect a greater or lesser number of vertebrae, including, two, three, five, six, seven, eight, or more vertebrae.

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the principles and features disclosed herein.

What is claimed is:

1. A method of delivering a rod to a plurality of spinal screws, comprising:
    advancing a rigid tissue penetrating member through heads of each of a plurality of spinal screws implanted into a plurality of adjacent vertebrae and tissue between adjacent spinal screws, wherein advancing includes direct advancement between the rigid tissue penetrating member and tissue between adjacent spinal screws;
    pulling the penetrating member to advance a cable and a rod through the heads of each of the screws and tissue between adjacent spinal screws, wherein the rod is detachably connected to a first end of the cable and the penetrating member is detachably connected with a second end of the cable; and
    selectively engaging the penetrating member with one or more pass members to direct the penetrating member between adjacent spinal screws and tissue between adjacent spinal screws.

2. The method of claim 1, wherein a single portion of the cable is advanced into a patient through, along or at an angle to a first tower extending from a first spinal screw, through the heads of each of the spinal screws, and out of the patient through, along or at an angle to a second tower extending from a second spinal screw.

3. The method of claim 1, wherein the direction of the advance of the rod through the heads of the spinal screws is the same as the direction of the advance of the cable through the heads of the spinal screws.

4. The method of claim 1, further comprising a rod puller configured to engage the cable and facilitate pulling of the rod into position within the receiving portions of the screws.

5. The method of claim 1, further comprising a penetrating member removal device configured to redirect a penetrating member such that further advancement of the penetrating member moves the penetrating member out of the patient's body.

6. The method of claim 1, wherein the cable comprises a plurality of regularly spaced markers.

7. A method of delivering a rod to a plurality of spinal screws, comprising:
    advancing a rigid tissue penetrating member through heads of each of a plurality of spinal screws and tissue between adjacent spinal screws, wherein each spinal screw comprises a threaded shaft and a head having a receiving portion, wherein advancing includes direct advancement between the rigid tissue penetrating member and tissue between adjacent spinal screws;
    pulling the penetrating member to advance a cable and a rod sized and shaped to be inserted into the receiving portions of the spinal screws, wherein the rod includes a first end detachably connected to a first end of the cable and the penetrating member is detachably connected with a second end of the cable;
    selectively engaging the penetrating member with one or more pass members, wherein one or more pass members are configured to advance the penetrating member from a receiving portion of a first pedicle screw to a receiving portion of a second pedicle screw and tissue between the first pedicle screw and second pedicle screw.

8. The method of claim 7, further comprising a rod puller configured to engage the cable and facilitate pulling of the rod into position within the receiving portions of the screws.

9. The method of claim 7, further comprising a penetrating member removal device configured to redirect a penetrating member such that further advancement of the penetrating member moves the penetrating member out of the patient's body.

10. A method of delivering a rod to a plurality of spinal screws, comprising:
    advancing a penetrating member through a cannula configured to facilitate insertion of a rod through the receiving portions of a plurality of spinal screws implanted into a plurality of adjacent vertebrae, wherein advancing includes direct advancement between the rigid tissue penetrating member and tissue between adjacent spinal screws;
    pulling the penetrating member to advance a cable and the rod through heads of each of the plurality of spinal screws and tissue between adjacent spinal screws, wherein the rod is sized and shaped to be inserted into the receiving portions of the spinal screws and wherein the rod is detachably connected to a first end of the cable and the penetrating member is detachably connected with a second end of the cable; and
    selectively engaging the penetrating member with one or more pass members to direct the penetrating member between adjacent spinal screws.

11. The method of claim 10, wherein the cannula is angularly positioned relative to the head of the screw.

12. The method of claim 10, further comprising a rod puller configured to engage the cable and facilitate pulling of the rod into position within the receiving portions of the screws.

13. The method of claim 10, further comprising a penetrating member removal device configured to redirect a penetrating member such that further advancement of the penetrating member moves the penetrating member out of the patient's body.

14. The method of claim 10, wherein the cable comprises a plurality of regularly spaced markers.

* * * * *